United States Patent [19]

Lafargue et al.

[11] Patent Number: 5,363,692
[45] Date of Patent: Nov. 15, 1994

[54] DEVICE AND METHOD FOR EVALUATING THE ABILITY OF A BODY CONTAINING A PRODUCT TO EXPEL THE PRODUCT FROM THE BODY

[75] Inventors: Eric Lafargue, Paris; Jean Espitalie, Le Vesinet; Thierry Lesage, Tessancourt sur Aubette, all of France

[73] Assignee: Institut Francais du Petrole, Rueil Malmaison, France

[21] Appl. No.: 583,321

[22] Filed: Sep. 17, 1990

[30] Foreign Application Priority Data

Sep. 15, 1990 [FR] France .................. 89 12150

[51] Int. Cl.⁵ ............................................ G01N 15/08
[52] U.S. Cl. ................................................... 73/38
[58] Field of Search ............ 73/19.12, 153, 38, 864.81

[56] References Cited

U.S. PATENT DOCUMENTS

| | | | |
|---|---|---|---|
| 2,296,852 | 9/1942 | Horner | 73/38 |
| 2,345,935 | 4/1944 | Hassler | 73/38 |
| 2,618,151 | 11/1952 | Leas | 73/38 |
| 2,713,789 | 7/1955 | Kelton | 73/38 |
| 3,023,606 | 3/1962 | Sarem | 73/38 |
| 3,152,471 | 10/1964 | Rahme et al. | 73/38 |
| 3,829,899 | 10/1974 | McMillen | 73/38 |
| 4,253,327 | 3/1981 | Wiley | 73/38 |
| 4,304,122 | 12/1981 | Tentor | 73/38 |
| 4,487,056 | 11/1984 | Wiley | 73/38 |
| 4,506,542 | 3/1985 | Rose | 73/38 |
| 4,643,019 | 2/1987 | Jones | 73/38 |
| 4,672,840 | 6/1987 | Cullick | 73/38 |
| 4,753,107 | 6/1988 | Reed et al. | 73/38 |
| 5,167,139 | 11/1992 | Lafargue et al. | 73/38 |

*Primary Examiner*—Hezron E. Williams
*Assistant Examiner*—Michael J. Brock
*Attorney, Agent, or Firm*—Antonelli, Terry, Stout & Kraus

[57] ABSTRACT

A device and method for enabling an evaluation of an ability of a body containing at least one product to expel at least a portion of the product. The body, for example, a rock sample is placed adjacent to a reservoir and a pressure gradient is effected between the body and the reservoir so as to result in at least a portion of the product being expelled from the body.

20 Claims, 1 Drawing Sheet

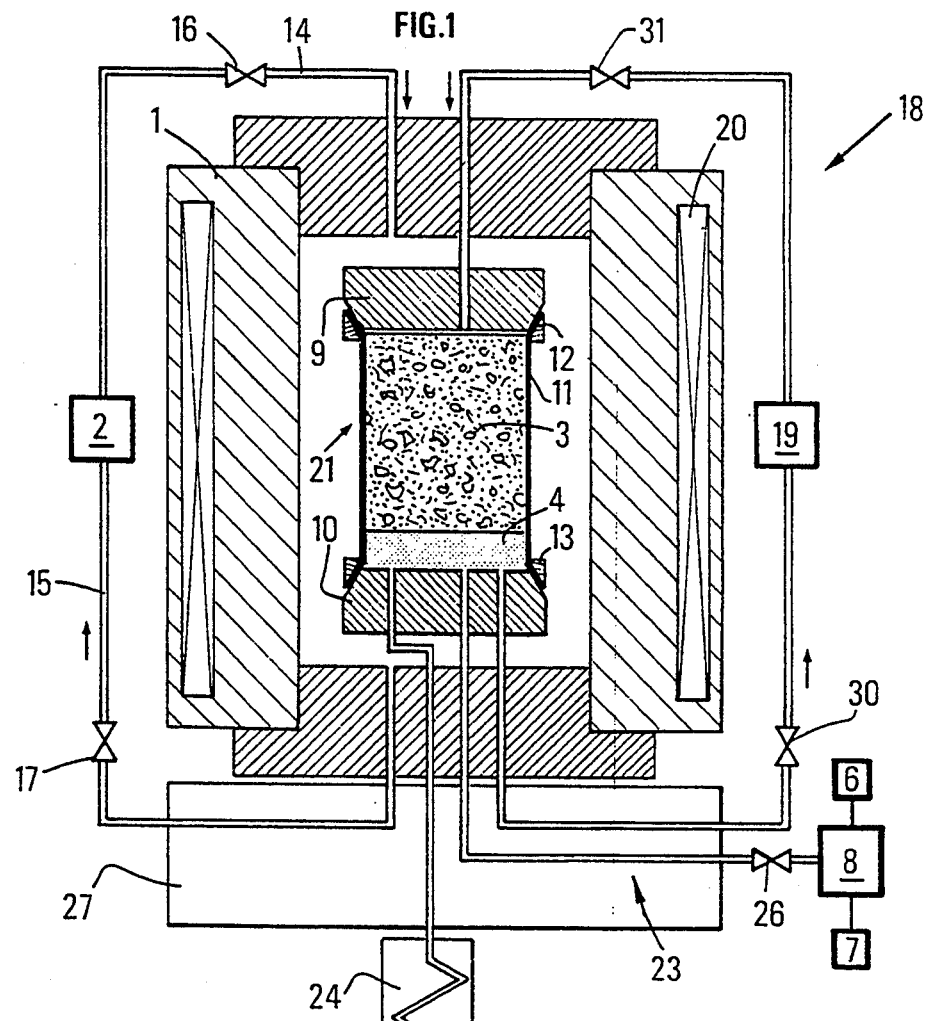
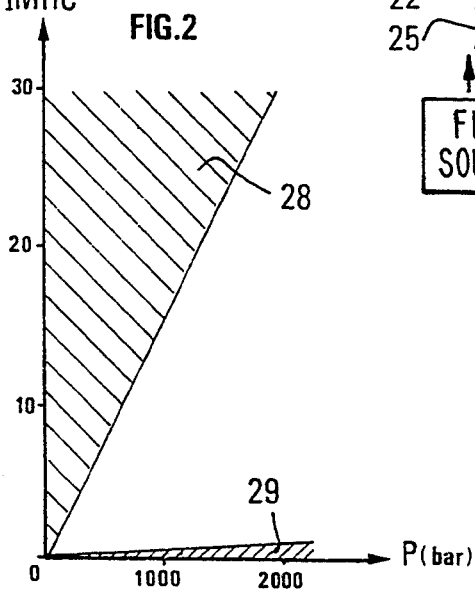
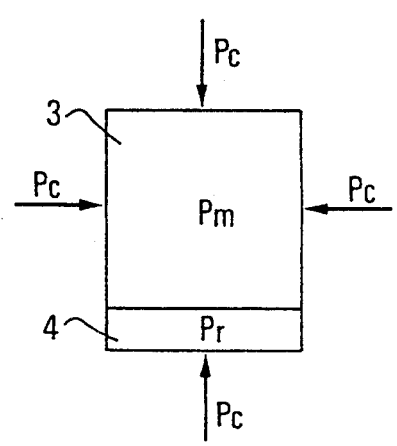

DEVICE AND METHOD FOR EVALUATING THE ABILITY OF A BODY CONTAINING A PRODUCT TO EXPEL THE PRODUCT FROM THE BODY

FIELD OF THE INVENTION

The present invention relates to an evaluation of an ability of a body containing at least one product to be expelled from the body and, more particularly, to rocks containing hydrocarbons.

BACKGROUND OF THE INVENTION

The characterization of parent rocks currently rests essentially on determining the quantity and quality of hydrocarbons likely to be generated when they are buried. Such a characterization is insufficient, since it does not take into account the ability the rocks possess to possibly expel the generated products. However, it is clear that, in a sedimentation basin, the presence of an oil (or gas) accumulation is strongly conditioned by the possibility the hydrocarbons originally possess for possibly leaving the parent rock containing these hydrocarbons.

The ability for expelling produced hydrocarbons seems to be an essential parameter in determining good parent rocks capable of easily expelling the hydrocarbons they have produced, as opposed to poor parent rocks capable of expelling fuel or no hydrocarbons. Currently, there are no means enabling this parameter to be defined. The present invention offers a method and device allowing the rocks to be classified according to their ability to expel hydrocarbons in accordance with the conditions of a migration test conducted on rock samples in the laboratory.

SUMMARY OF THE INVENTION:

Generally speaking, the present invention therefore relates to a method for assessing the ability of a body to expel a product it contains, with the method comprising the steps of placing a body and a reservoir adjacently, effecting a pressure gradient between the reservoir and the body so that the gradient provokes an expulsion of at least one part of the product towards the reservoir, and analyzing a portion of the product recovered in the reservoir.

The analysis of the portion of the product recovered in the reservoir can be carried out by continuously sweeping the reservoir.

The method of the invention may also comprise a step of heating the body and/or a step of pressurizing the body.

The above-mentioned analysis could be a qualitative analysis and/or a quantative analysis of the product.

The method of the invention may comprise determination of a migration criterion linked to the ratio of the amount of the expelled product in proportion to the quantity of the initially treated body.

The method and device of the invention may be applied to assessing the amount of hydrocarbon contained in a rock sample.

Similarly, the method and device of the present invention may be applied to assess the product amount other than the hydrocarbons contained in the rock sample such as, for example, water, carbon monoxide, carbon dioxide or sulfur dioxide.

The present invention also relates to a device for assessing the ability of a body containing at least one product to be expelled from the body, with the device comprising a high pressure chamber containing a confinement medium, and means for generating a confinement pressure. An assembly or test piece is hermetically isolated from the confinement medium, with the assembly comprising a sample of the body and a reservoir.

The device may comprise a means for controlling the pressure gradient existing between the sample and the reservoir.

The sweeping means may comprise means for detecting and/or analyzing the fluid selected by sweeping in the reservoir.

The device of the invention may comprise means for controlling the temperature of the sweeping fluids.

The device of the invention may comprise mainly a chamber or high pressure cell in which an assembly, constituted by a rock assembly, is placed in a reservoir superimposed or juxtaposed in an assembly hermetically isolated from the confinement medium, preferably, by a metal jacket and two steel stoppers. In the remainder of the text, this assembly will simply be referred to as a "test piece". Under the effect of the confinement pressure the fluids present in the rock sample are expelled towards the reservoir where a sweeping system is subsequently able to transfer the fluids to specific detectors, thereby enabling the expelled products to be continuously analyzed.

The novelty of the present invention essentially resides in the juxtaposition of the rock sample and the reservoir in an hermetic assembly in relation to the confinement medium. In addition, the invention resides in the continuous analysis of the products expelled with the aid of a sweeping device. In the latter case, it is thus possible to analyze the kinetics of the expulsion, which would not be possible if the cell had to be dismantled after each experiment.

BRIEF DESCRIPTION OF THE DRAWINGS

The present invention shall be more readily understood and its advantages appear more clearly from the following description of a particular example, in no way restrictive, applied to the case of oil-bearing rocks, shown in the accompanying drawings, wherein:

FIG. 1 is a partial schematic cross-sectional view of a device according to the present invention;

FIG. 2 is a graphical illustration of characteristics enabling the rocks to be classified; and FIG. 3 is a schematic diagram of a manner by which pressures are applied to the rock sample and the reservoir.

DETAILED DESCRIPTION

Referring now to the drawings wherein like reference numerals are used throughout the various views to designate like parts and, more particularly, to FIG. 1, according to this figure, the device of the present invention includes a high pressure chamber body 1 provided with a furnace 20 making it possible to work under pressures of generally between 1 and 4,000 bars and temperatures of generally between 20 and 40° C., and with the furnace 20 being adapted to be possibly integrated with the high pressure chamber body 1. Confinement pressure generating means 2 are provided, and an assembly or test piece generally designated by the reference numeral 21 is hermetically isolated from the confinement medium during tests. The assembly or test piece 21 is adapted to receive a rock sample 3 to be tested in a reservoir 4.

Means 19 are provided for controlling the pressure gradient between the rock sample 3 and the reservoir 4, with means 35 sweeping the products expelled in the reservoir 4 and/or specific detectors 6, 7 containing hydrocarbons and possibly $CO_2$, CO and $H_2O$ being connected to a sampling loop 8.

The assembly or test piece 21 contains the rock sample 3 and the reservoir 4 which are maintained in a juxtaposed position and isolated from the confinement medium by two metal stoppers 9, 10 and a metal jacket 11 folded onto the stoppers with the aid of two metal rings 12, 13 possibly having a corner-shaped cross-section. The confinement pressure generating means 2 are connected to the chamber by pipes 14, 15 comprising valves 16, 17. The valves 16, 17 make is possible to isolate the confinement medium from the confinement pressure generation means 2 and to subsequently empty the confinement chamber at the time of stopping the confinement pressure generation means 2.

Gradient control means generally designated by the reference numeral 18 control and subsequently create the pressure gradient in the test piece 21, with these means 18 comprising, for example, a pump and, possibly, valve control means 30, 31, in particular, for isolating the internal space of the test piece 21 from the pump 19.

The gradient control means 18 controlling the pressure gradient between the rock sample 3 and the reservoir 4 conventionally comprise a differential pressure sensor connected to a pressure control system controlling a pneumatic pump. These gradient control means 18 include valve control means designated by the reference numeral 19. The gradient control means 18 are different from the confinement pressure generating means 2.

The confinement pressure generating means 2 may comprise one or more conventional pneumatic pumps associated with control systems connected to a pressure sensor measuring the pressure existing in the confinement chamber.

The sweeping means 35 may comprise a sweeping fluid source 40 and an input circuit 22 bringing the sweeping fluid supplied by the fluid source 40 to the reservoir 4 through the stopper 10, and an output circuit 23 bringing the sweeping fluid to the sampling loop 8 after the sweeping fluid has passed through the reservoir 4.

The input circuit 22 may comprise heating means making it possible to heat the sweeping fluid, and the sweeping circuit may comprise valves 25, 26 making it possible to stop the circulation of the sweeping fluid.

So as to avoid condensation in the pipe of the output circuit 23 of the sweeping means 35, the pipe may be arranged, at least over most of its length, so as to extend into a thermal regulated assembly 27. The other pipes may also partially extend into the thermal regulated assembly 27, as shown in FIG. 1.

The device of the invention makes it possible to carry out expulsion tests on samples of natural rocks, cores or plugs. The diameters of these samples may be between 20 and 50 mm for a length of between 20 and 55 mm. The rocks used may be immature (i.e. not having generated any hydrocarbons at the time they are buried) or mature rock samples.

As regards the first case, prior to the expulsion test, the generation of hydrocarbons shall be carried out in accordance with the appropriate temperature and pressure conditions in the high pressure chamber, for example, at a temperature of between 300° and 400° C. and a pressure approaching 1,000 bars for forty-eight to seventy-two hours. The products expelled in accordance with these temperature conditions in the reservoir 4 during this phase may be exploited so as to assess the migration ability of the hydrocarbons in the sample, as well as the quality of the artificial maturity operation. However, for simple exploitation of information, it is preferable to eliminate them from the reservoir 4, for example, either with the aid of the sweeping system or by changing the reservoir 4. This is obtained by opening the assembly or test piece 21 and producing a new assembly or test piece containing the artificially mature rock and a new reservoir. The actual expulsion test may thus be carried out on the artificially mature rock.

With regard to a mature rock, only the expulsion test is required, given the fact that the mature rock has already naturally generated hydrocarbons at the time the rock is buried.

The expulsion test includes analyzing the amount and type of products expelled in the reservoir 4 during the time involved in accordance with the pressure and temperature conditions of the test. The reservoir 4 may contain a natural rock (sandstone, carbonate, etc.) or any porous material (metallic frit, ceramic). The thickness of the reservoir 4 may vary between 2 to 20 mm. The reservoir 4 may be originally empty or may contain water.

In the embodiment described in connection with FIG. 1, once expelled from the reservoir 4, the products are directed to the various detectors 6, 7 by the sweeping system introducing a heated liquid (inert gases, water with or without surface-active agents, $CO_2$, organic solvents). The assembly 21 is heated with the aid of the thermoregulated assembly 27 so as to avoid cold points appearing on the output sweeping circuit 23 where the expelled products could be subjected to condensation, thus falsifying the quantative analysis. At the output of the sample loop 8, the hydrocarbons, water, CO, $CO_2$ and the $H_2S$ are separately analyzed.

The device of the invention is extremely flexible and makes it possible to conduct expulsion tests in various modes, that is, confinement pressure alone or with an additional pressure gradient imposed between the rock sample 3 and the reservoir 4. If need be, the sweeping system may also be interrupted if it is desired to recover the product expelled only at the end of the experiment rather than continuously expelling the product.

The temperature and pressure ranges may be extended from 20° to 400° C. and from 100 to 4,000 bar. The pressures and temperatures may be recorded automatically and may be time programmed.

As already stated, the experimental device makes it possible to assess the ability of a rock sample to expel, in particular, hydrocarbons, water, CO, $CO_2$ and $H_2S$ it was able to generate at the time it was buried. With the aid of the definition of a migration index (IMHC), it is possible, according to the invention, to classify the parent rocks into extremely good parent rocks, that are able to easily expel the formed hydrocarbons, as opposed to poor parent rocks unable to expel to any significant extent the hydrocarbons they have generated.

The IMHC index may, for example, be defined as follows:

IMHC=Q HC expelled (mg)/100 g initial rock, where:

Q=quantity of product expelled from the rock.

The graph of FIG. 2 is established on the basis of experiments on various rocks and seventy-two hours was selected as an average period for the experiments, with the confinement pressure, in bars, being shown along the abscissa and the IMHC along the ordinate. The zone 28 corresponds to good parent rocks, that is, rocks easily expelling the hydrocarbons they contain. On the other hand, the zone 29 corresponds to poor parent rocks. It is of course possible to give other similar graphs for other experimental time periods.

In parallel with the definition of the Migration Index of Hydrocarbons, it is possible to define similar indices for other expelled products such as, for example, the following indices:

$IMH_2O = QH_2O$ (mg)/100 g initial rock;
$IMCO + QCO$ (mg)/100 g initial rock;
$IMCO_2 = QCO$ (mg)/100 g initial rock; and
$IMH_2S = QH_2S$ (mg)/100 g initial rock.

Finally, the expulsion kinetics determined from a continuous analysis of the expelled products makes it also possible to characterize the ability of the tested rock samples and expelling the time-formed products at the time they are buried in the sedimentation layer basins.

FIG. 3 diagrammatically illustrates the pressures to which the rock sample 3 and reservoir 4 are subjected.

In FIG. 3, PC represents the confinement pressure applied to both the skeleton of the rock sample 3 and the reservoir 4. The pressure PC substantially corresponds to the pressure existing in the chamber, at least when the resistance power of the metal jacket 11 is negligible with respect to the stresses generated by the confinement pressure. Pm represents the pressure in the pores of the parent rock which also called the pressure in the parent rock, and Pr represents the pressure in the pores of the reservoir 4 or the pressure in the reservoir 4.

The pressure gradient corresponds to the difference of Pm-Pr, and it is this pressure gradient which makes it possible to expel fluids from the rock sample 3. As mentioned above, the pressure gradient may be controlled by the pressure gradient control means 19 or may be simply generated due to the confinement pressure and the mechanical characteristic differences between the parent rock sample 3 and the reservoir 4, with the reservoir 4 being the most resistant.

At the start of the test, the tank 4 may be empty or full of fluid, such as water. If filled with water with an initial pressure $P_m$, a fluid pressure $P_r$ is preferably imposed in the tank 4 so that the gradient $\Delta P = P_m - P_r$, namely, near the natural pressure gradient, that is, generally less than 1,000 bars.

Another advantage of filling the reservoir with water is that it is possible to allow for control of the pressure gradient during the artificial generation of fluids in the immature parent rocks at high temperatures (300°–400° C.) and which generates high fluid pressures.

The reservoir 4 may be a natural rock (sandstone, porous carbonate, volcanic rock, etc.) or a porous synthetic material (metallic frit, ceramic . . . ).

The tank porosity / parent rock porosity (preferably tested) ratio must not be less than 4 at the beginning of the experiment, and the jacket 11 may be made of copper.

What is claimed is:

1. A method for evaluating an ability of a rock sample containing a product to expel the product from the rock sample, the method comprising the steps:

placing said rock sample in juxtaposition to a reservoir;

providing a pressure gradient between the reservoir and the rock sample to cause expulsion of at least a portion of said product into said reservoir; and analyzing the portion of the product expelled from the rock sample into the reservoir to evaluate an ability of the rock sample to expel the product by determining a migration criterion in accordance with a ratio of an amount of the expelled product to an amount of the rock sample as initially treated.

2. A method in accordance with claim 1 wherein:
the product is a hydrocarbon contained in the rock sample.

3. A method in accordance with claim 1 wherein:
the product is at least one of water, carbon monoxide and sulfur dioxide contained in the rock sample.

4. A method for evaluating an ability of a body containing a product to expel the product from the body, the method comprising the steps:

placing said body in juxtaposition to a reservoir;

providing a pressure gradient between the reservoir and the body to cause expulsion of at least a portion of said product into said reservoir;

sweeping said reservoir with a fluid to remove from said reservoir at least some of the product expelled into said reservoir; and analyzing the product removed from said reservoir by sweeping to evaluate an ability of the body to expel the product by determining a migration criterion.

5. A method according to claim 4, wherein the step of analyzing includes continuously sweeping the product from said reservoir.

6. A method according to one of claims 4 or 5, further comprising the step:

pressurizing said body to a predetermined pressure with a pressure gradient between said reservoir and said body.

7. A method according to claim 6, further comprising the step:

heating the body to a predetermined temperature.

8. The method according to claim 7, wherein the predetermined temperature is in a range of 20° C. to 400° C.

9. A method according to claim 6, wherein the step of analyzing comprises:

carrying out at least one of a qualitative and quantative analysis of the product expelled from the body.

10. A method according to claim 6, wherein the predetermined pressure is in a range of 1 to 4000 bar.

11. A method according to one of claims 4 or 5, wherein the step of analyzing comprises:

carrying out at least one of a qualitative and quantative analysis of the product expelled from the body.

12. A method according to one of claims 4 or 5, wherein;

the body is a rock sample, and the product is hydrocarbon contained in the rock sample.

13. A method according to one of claims 4 or 5, wherein:

the body is a rock sample, and the product is at least one of water, carbon monoxide, carbon dioxide and sulfur dioxide contained in the rock sample.

14. A device for enabling an evaluation of an ability of a body containing at least one product to expel the product from said body, the device comprising:

a high pressure chamber including a confinement medium;

confinement pressure generation means for generating a pressure gradient in the confinement medium in said pressure chamber; and an assembly disposed in said high pressure chamber, hermetically isolated from the confinement medium and including said body and a reservoir adjacent said body, with said pressure gradient causing expulsion of at least a portion of the at least one product contained in said body into said reservoir;

means for sweeping said reservoir with a sweeping fluid to remove from said reservoir at least some of the at least a portion of the at least one product expelled into said reservoir from said body; and means for analyzing the product removed from said reservoir by sweeping to evaluate an ability of the body to expel the product by determining a migration criterion.

15. A device according to claim 14 further comprising:

means for controlling a pressure gradient between said body and said reservoir.

16. A device according to claim 15 further comprising:

means for controlling a temperature of the sweeping fluid.

17. A device according to claim 16 further comprising:

means for controlling a temperature of the sweeping fluid.

18. A device according to one of claims 14 or 15 further comprising:

means for at least one of detecting or analyzing the product removed by scanning said reservoir.

19. A device according to one of claims 14 or 15 wherein said means for scanning includes:

a fluid source for supplying the sweeping fluid to said assembly and a means for sampling the sweeping fluid.

20. A device according to claim 14 further comprising:

means for at least one of detecting and analyzing fluids collected by sweeping said reservoir.

* * * * *